United States Patent [19]

Takasugi et al.

[11] Patent Number: 5,059,608
[45] Date of Patent: Oct. 22, 1991

[54] BICYCLIC AMINE COMPOUND AND A PROCESS FOR THE PREPARATION THEREOF

[75] Inventors: Hisashi Takasugi; Atsushi Kuno, both of Osaka; Mitsuru Ohkubo, Hyogo, all of Japan

[73] Assignee: Fujisawa Pharmaceutical Company, Ltd., Osaka, Japan

[21] Appl. No.: 327,813

[22] Filed: Mar. 23, 1989

[30] Foreign Application Priority Data

Apr. 5, 1988 [GB] United Kingdom ............ 8807922.3

[51] Int. Cl.$^5$ .................. A61K 31/47; C07D 401/04
[52] U.S. Cl. .................. 514/307; 514/235.2; 514/254; 540/593; 544/128; 544/363; 546/139; 546/144; 546/146
[58] Field of Search ............ 546/144, 146, 139; 514/307, 235.2; 540/593; 544/363, 128

[56] References Cited

U.S. PATENT DOCUMENTS 3,963,725 6/1976 Kishimoto et al. ............ 546/139
3,978,063 8/1976 Kishimoto et al. ............ 546/139

FOREIGN PATENT DOCUMENTS 0230871 8/1987 European Pat. Off. .

OTHER PUBLICATIONS

Bersch et al. (I), "Chemical Abstracts", vol. 90, 1979, col. 90:121374s.
Bersch et al. (II), "Chemical Abstracts", vol. 97, 1982, col. 97:162796u.

Primary Examiner—Frederick E. Waddell
Assistant Examiner—James H. Turnipseed
Attorney, Agent, or Firm—Oblon, Spivak, McClelland, Maier & Neustadt

[57] ABSTRACT

The invention relates to a compound useful as an anticonvulsant, and for treatment of delayed neuronal death, the compound being a bicyclic amine of the formula:

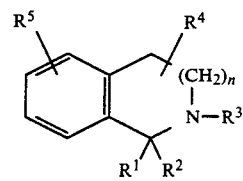

wherein
$R^1$ is lower alkyl,
$R^2$ is aryl which may have one or more suitable substituent(s), cyclo(lower)alkyl or heterocyclic group,
$R^3$ is hydrogen, lower alkyl which may have one or more suitable substituent(s), lower alkenyl, or acyl which may have one or more suitable substituent(s),
$R^4$ is hydrogen, lower alkyl, or hydroxy(lower)alkyl,
$R^5$ is hydrogen, lower alkyl, halogen, or protected amino, and
n is an integer of 1 or 2, with the proviso that when $R^3$ is lower alkyl which may have one or more suitable substituent(s), $R^2$ is cyclo(lower)alkyl or heterocyclic group,
or a pharmaceutically acceptable salt thereof.

14 Claims, No Drawings

BICYCLIC AMINE COMPOUND AND A PROCESS FOR THE PREPARATION THEREOF

The present invention relates to novel bicyclic amine compound and a pharmaceutically acceptable salt thereof.

More particularly, it relates to novel bicyclic amine compound and a pharmaceutically acceptable salt thereof, which is an N-methyl-D-aspartate (an excitatory amino acid) receptor antagonist and useful as an anticonvulsant and a drug for treatment of the delayed neuronal death induced, for instance, by cerebral ischemia, for example, in case of cardiac arrest, to a process for the preparation thereof, to a pharmaceutical composition comprising the same, and to a use of the same as a medicament in treatment of convulsion and delayed neuronal death in human being or animal.

Accordingly, one object of the present invention is to provide novel bicyclic amine compound and a pharmaceutically acceptable salt thereof, which is useful as stated above.

Another object of the present invention is to provide a process for the preparation of novel bicyclic amine pound and a salt thereof.

A further object of the present invention is to provide a pharmaceutical composition comprising, as an active ingredient, said bicyclic amine compound or a pharmaceutically acceptable salt thereof.

Still further object of the present invention is to provide a use of said bicyclic amine compound and a pharmaceutically acceptable salt thereof as a medicament in the treatment of convulsion and delayed neuronal death in human being or animal.

The object bicyclic amine compound of the present invention is novel and can be represented by the following general formula (I).

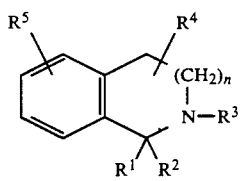

wherein
  $R^1$ is lower alkyl,
  $R^2$ is aryl which may have one or more suitable substituent(s), cyclo(lower)alkyl or heterocyclic group,
  $R^3$ is hydrogen, lower alkyl which may have one or more suitable substituent(s), lower alkenyl, or acyl which may have one or more suitable substituent(s),
  $R^4$ is hydrogen, lower alkyl, or hydroxy(lower)alkyl,
  $R^5$ is hydrogen, lower alkyl, halogen, or protected amino, and
  n is an integer of 1 or 2.

According to the present invention, the novel bicyclic amine compound (I) can be prepared by the processes illustrated in the following reaction schemes.

Process 1

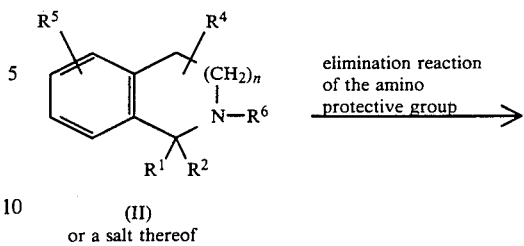

Process 2

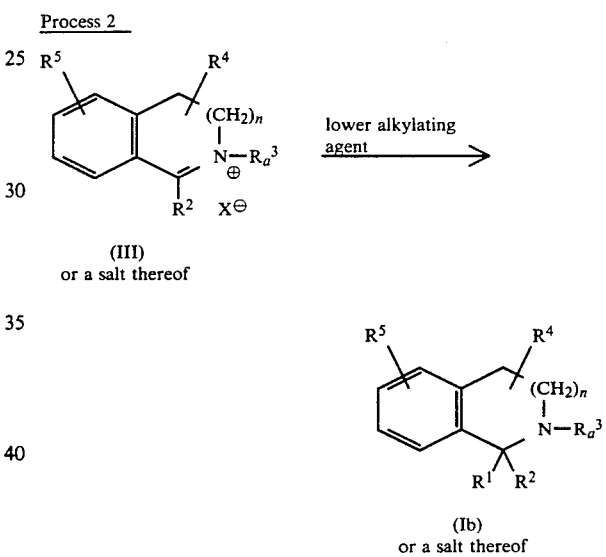

Process 3

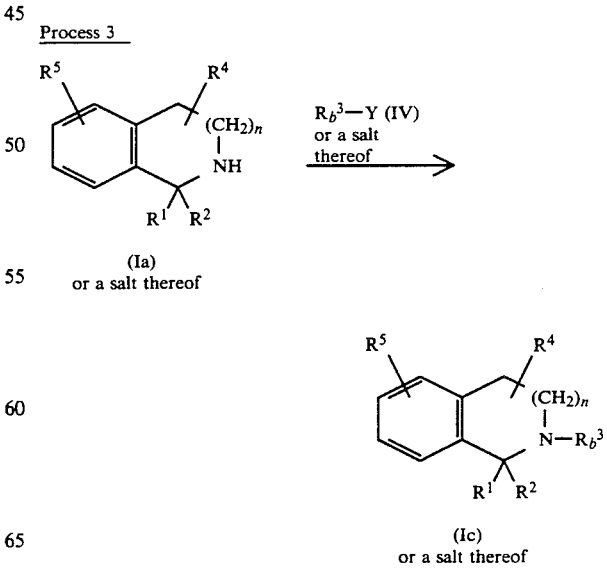

Process 4

-continued

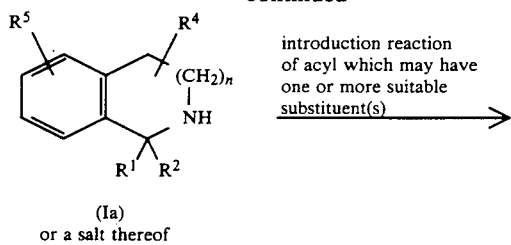

(Ia)
or a salt thereof

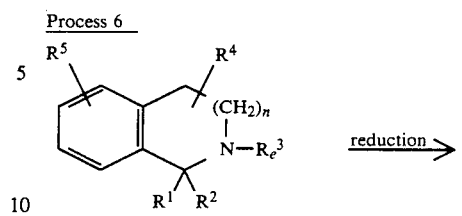

(If)
or a salt thereof

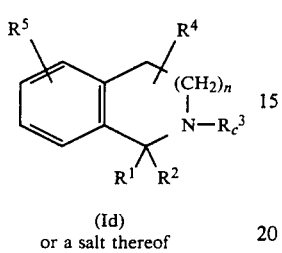

(Id)
or a salt thereof

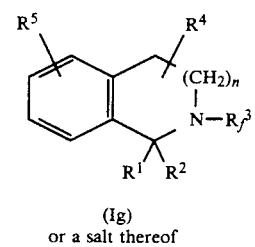

(Ig)
or a salt thereof

Process 5

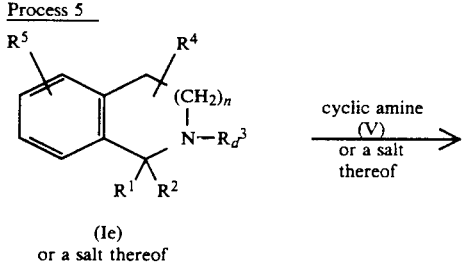

(Ie)
or a salt thereof

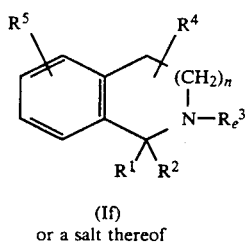

(If)
or a salt thereof wherein
$R^1$, $R^2$, $R^4$, $R^5$ and n are each as defined above,
$R_a^3$ is lower alkyl which may have one or more suitable substituent(s), lower alkenyl, or acyl which may have one or more suitable substituent(s),
$R_b^3$ is lower alkyl which may have one or more suitable substituent(s), or lower alkenyl,
$R_c^3$ is acyl which may have one or more suitable substituent(s),
$R_d^3$ is lower alkanoyl having halogen,
$R_e^3$ is lower alkanoyl having cyclic amino,
$R_f^3$ is lower alkyl having cyclic amino,
$R^6$ is amino protective group,
$X^\ominus$ is an anion, and
Y is a leaving group.

The starting compounds (II) and (III) to be used in these processes are novel and can be prepared by the processes illustrated in the following reaction schemes.

Process For The Preparation of The Starting Compound (II)

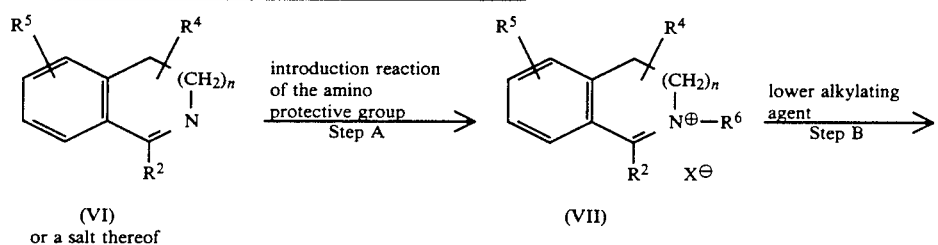

Process For The Preparation of The Starting Compound (III)

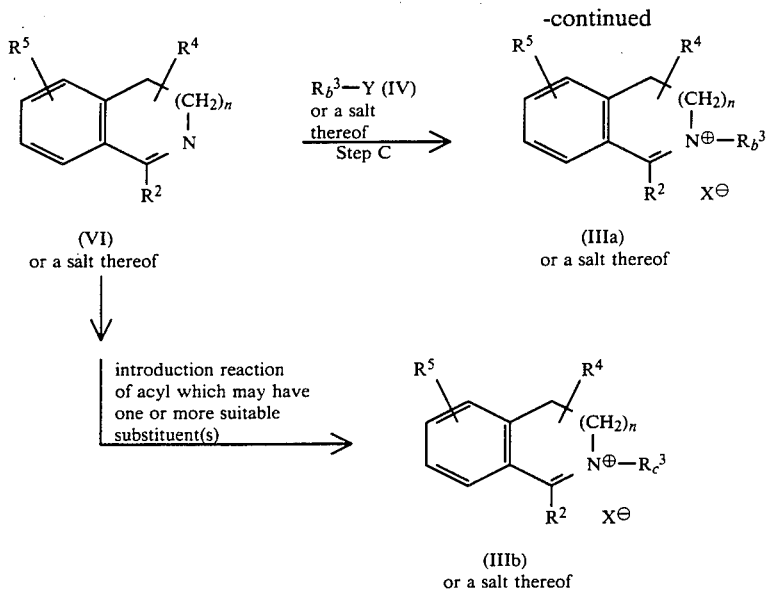

(VI)
or a salt thereof

↓ introduction reaction of acyl which may have one or more suitable substituent(s)

(IIIb)
or a salt thereof wherein $R^1$, $R^2$, $R_b^3$, $R_c^3$, $R^4$, $R^5$, $R^6$, n, $X^\ominus$ and Y are each as defined above.

The object compound (I), (Ia), (Ib), (Ic), (Id), (Ie), (If), (Ig) and the starting compound (II) include stereomers due to the existence of the asymmetric carbon atom therein. Said stereomers are also included within the scope of the present invention.

Suitable pharmaceutically acceptable salt of the object compound (I) is a conventional non-toxic salt and may include an acid addition salt such as an organic acid salt (e.g., acetate, trifluoroacetate, maleate, tartrate, methanesulfonate, benzenesulfonate, formate, toluenesulfonate, etc.), an inorganic acid salt (e.g. hydrochloride, hydrobromide, hydriodide, sulfate, phosphate, etc.), a salt with an amino acid (e.g. arginine, aspartic acid, glutamic acid, etc.), or the like.

In the above and following descriptions of the present specification suitable example and illustrations of the various definitions which the present invention include within the scope thereof are explained in detail as follows.

The term "lower" is intended to mean 1 to 6 carbon atom(s) unless otherwise indicated.

Suitable "lower alkyl" may include straight or branched ones such as methyl, ethyl, propyl, isopropyl, butyl, tert-butyl, pentyl, hexyl or the like, in which the preferred one may be $(C_1-C_4)$alkyl and the most preferred one may be methyl and ethyl.

Suitable example of "suitable substituent(s)" in "lower alkyl which may have one or more suitable substituent(s)" may include aryl (e.g. phenyl, naphthyl, pentalenyl, indenyl, etc.), cyclic amino such as 5- or 6-;membered one having at least one nitrogen atom (e.g. 1-pyrrolidinyl, 1-imidazolidinyl, 1-pyrrolinyl, piperidino, 1-piperazinyl, morpholino, etc.) and the like.

Suitable "lower alkyl which may have one or more suitable substituent(s)" may include lower alkyl as mentioned above which may have one or more (preferably 1 to 3) suitable substituent(s) as mentioned above, in which the preferred one may be lower alkyl, lower alkyl having aryl and lower alkyl having cyclic amino, the more preferred one may be lower alkyl, lower alkyl having phenyl and lower alkyl having 6-membered cyclic amino, the much more preferred one may be $(C_1-C_4)$alkyl, $(C_1-C_4)$alkyl having phenyl and $(C_1-C_4)$alkyl having piperidino, and the most preferred one may be methyl, ethyl, phenethyl and 2-piperidinoethyl.

Suitable "aryl" in "aryl which may have one or more suitable substituent(s)" may include phenyl, naphthyl pentalenyl, indenyl, and the like, and suitable example of "suitable substituent(s)" in this group may include lower alkyl as mentioned above, lower alkoxy (e.g. methoxy, ethoxy, propoxy, butoxy, t-butoxy, pentyloxy, hexyloxy, etc.), halogen (e.g. fluoro, chloro, bromo and iodo) and the like.

The preferred "aryl which may have one or more suitable substituent(s)" may be phenyl which may have 1 to 3 suitable substituent(s) selected from a group consisting of lower alkyl, lower alkoxy and halogen, the more preferred one may be phenyl, phenyl having lower alkyl (e.g. o-tolyl, m-tolyl, p-tolyl, 2-ethylphenyl, 3-propylphenyl, 4-butylphenyl, 3-t-butylphenyl, 4-pentylphenyl, 2-hexylphenyl, etc.), phenyl having lower alkoxy (e.g. 2-methoxyphenyl, 4-methoxyphenyl, 3-ethoxyphenyl, 4-propoxyphenyl, 2-butoxyphenyl, 3-t-butoxyphenyl, 2-pentyloxyphenyl, 4-hexyloxyphenyl, etc.) and phenyl having halogen (e.g. 2-fluorophenyl, 3-fluorophenyl, 4-fluorophenyl, 2-chlorophenyl, 3-chlorophenyl, 4-chlorophenyl, 2-bromophenyl, 4-iodophenyl, etc.), and the most preferred one may be phenyl, p-tolyl, 4-methoxyphenyl, 3-fluorophenyl, 4-fluorophenyl, 2-chlorophenyl, 3-chlorophenyl and 4-chlorophenyl.

Suitable "cyclo(lower)alkyl" may include cyclopropyl, cyclobutyl, cyclopentyl and cyclohexyl, in which the preferred one may be cyclo($C_4-C_6$) and the more preferred one may be cyclohexyl.

Suitable "heterocyclic group" may be the conventional ones having at least one hetero atom such as oxygen, sulfur, nitrogen or the like and suitable example thereof may include unsaturated 5- or 6-membered ones having 1 to 3 hetero atom(s) such as furyl, thienyl, pyrrolyl, thiazolyl, isothiazolyl, isoxazolyl, dioxolyl (e.g. 1,3-dioxolyl, etc.), dithiolyl (e.g. 1,3-dithiolyl, etc.), 1,2-oxathiolyl (e.g. 3H-1,2-oxathiolyl, etc.), pyrazolyl, 2,3-dihydrofuryl, 2,3-dihydrothienyl, pyrrolinyl, 4,5-dihydrothiazolyl, thiadiazolyl (e.g., 1,2,4-thiadiazolyl, etc.), pyranyl (e.g. 2H-pyranyl, etc.), thiinyl (e.g. 4H- thiinyl, etc.), pyridyl, 1,3-oxathiinyl (e.g. 4H-1,3-oxathiinyl, etc.), 1,4-dioxinyl, 1,3-dithiinyl (e.g. 6H-1,3-dithiinyl, etc.), 1,3-oxazinyl (e.g. 6H-1,3-oxazinyl, etc.), 1,4-thiazinyl (e.g. 2H-1,4-thiazinyl, etc.), pyrimidinyl, 1,2,5-thiadiazinyl (e.g. 6H-1,2,5-thiadiazinyl, etc.), or the like;

saturated 5- or 6-membered ones having 1 to 3 hetero atom(s) such as oxolanyl, thiolanyl, pyrrolidinyl, thiazolidinyl (e.g. 1,3-thiazolidinyl, etc.), oxathiolanyl (e.g. 1,2-oxathiolanyl, etc.), isoxazolidinyl, 1,3-dioxolanyl, 1,3-dithiolanyl, 1,3,4-dioxathiolanyl, oxanyl, dioxanyl (e.g. 1,4-dioxanyl, etc.), dithianyl (e.g. 1,3-dithianyl, etc.), 1,3,5-oxadithianyl, piperidyl, piperazinyl, perhydro-1,4-thiazinyl, perhydro-1,3-oxazinyl, perhydro-1,2,5-thiadiazinyl, or the like; and the like, in which the preferred one may be unsaturated 5- or 6-membered heterocyclic group having 1 to 3 oxygen or sulfur atom(s), the more preferred one may be unsaturated 5-membered heterocyclic group having 1 to 2 oxygen or sulfur atom(s) and the most preferred one may be furyl and thienyl.

Suitable "lower alkenyl" may include straight or branched ones having 2 to 6 carbon atoms such as vinyl, allyl, isopropenyl, 2-butenyl, 4-pentenyl, 1-hexenyl or the like, in which the preferred one may be ($C_2$–$C_4$)alkenyl and the most preferred one may be allyl.

Suitable "acyl" may include lower alkanoyl (e.g. formyl, acetyl, propionyl, butyryl, valeryl, pivaloyl, hexanoyl, etc.), lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc.), and the like and said "acyl" may have one or more (preferably 1 to 3) suitable substituent(s) such as aforesaid halogen, aforesaid cyclic amino, or the like.

The preferred "acyl which may have one or more suitable substituent(s)" may be lower alkanoyl, lower alkanoyl having halogen, lower alkanoyl having cyclic amino, the more preferred one may be lower alkanoyl having halogen and lower alkanoyl having 6-membered cyclic amino, the much more preferred one may be ($C_2$–$C_4$)alkanoyl having halogen and ($C_2$–$C_4$)alkanoyl having piperidino, and the most preferred one may be 2-chloroacetyl and 2-piperidinoacetyl.

Suitable "hydroxy(lower)alkyl" may include hydoxymethyl, 2-hydroxyethyl, 2-hydroxypropyl, 1-hydroxybutyl, 1-hydroxymethyl-1-methylethyl, 3-hydroxypentyl, 6-hydroxyhexyl, in which the preferred one may be hydroxy($C_1$–$C_4$)alkyl and the more preferred one may be hydroxymethyl.

Suitable "protected amino" may be amino group protected by conventional amino protective group such as ar(lower)alkyl as explained below, aforesaid acyl or the like, in which the preferred one may be lower alkoxycarbonylamino (e.g. methoxycarbonylamino, ethoxycarbonylamino, propoxycarbonylamino, butoxycarbonylamino, t-butoxycarbonylamino, pentyloxycarbonylamino, hexyloxycarbonylamino, etc.), the more preferred one may be ($C_1$–$C_4$)alkoxycarbonylamino and the most preferred one may be ethoxycarbonylamino.

Suitable "amino protective group" may be conventional ones to be used in this field of the art and, for example, may include ar(lower)alkyl such as phenyl(lower)alkyl (e.g. benzyl, phenethyl, etc.), diphenyl(lower)alkyl (e.g. benzhydryl, etc.), triphenyl(lower)alkyl (e.g. trityl, etc.) or the like, each of which may have aforesaid lower alkoxy; and the like, in which the preferred one may be phenyl(lower)alkyl which may have lower alkoxy, the more preferred one may be phenyl($C_1$–$C_4$)alkyl which may have ($C_1$–$C_4$)alkoxy and the most preferred one may be benzyl and 4-methoxybenzyl.

Suitable "anion" may be formate, acetate, trifluoroacetate, maleate, tartrate, methanesulfonate, benzenesulfonate, toluenesulfonate, halogen anion (e.g. chloride, bromide, iodide), sulfate, phosphate, or the like.

Suitable "a leaving group" may include halogen as mentioned before, acyloxy such as lower alkanoyloxy (e.g. acetoxy, etc.), sulfonyloxy (e.g. mesyloxy, tosyloxy, etc.) or the like, and the like.

The processes for preparing the object compound (I) of the present invention are explained in detail in the following.

Process 1

The compound (Ia) or a salt thereof can be prepared by subjecting the compound (II) or a salt thereof to elimination reaction of the amino protective group.

Suitable salts of the compounds (Ia) and (II) can be referred to the ones as exemplified for the compound (I).

This reaction is carried out in accordance with a conventional method such as hydrolysis, reduction, oxydation or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]-undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any, other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the abovementioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, acetic acid, etc., or a mixture thereof.

The reaction temperature of this reduction is not critical and the reaction is usually carried out under cooling to warming.

The oxydation method applicable for the elimination reaction may include oxydation using an oxydating agent such as cerium compound (e.g. ceric ammonium nitrate, etc.) or the like.

The oxydation is usually carried out in a conventional solvent such as water, alcohol (e.g. methanol, ethanol, etc.), acetonitrile or any other solvent which does not adversely influence the reaction.

The reaction temperature of this oxydation is not critical and the reaction is usually carried out under cooling to warming.

Process 2

The compound (Ib) or a salt thereof can be prepared by reacting the compound (III) or a salt thereof with a lower alkylating agent.

Suitable salts of the compounds (Ib) and (III) can be referred to the ones as exemplified for the compound (I).

Suitable examples for said lower alkylating agent may be so-called Grignard type reagent shown in the formula: $R^1MgY$ (wherein $R^1$ is lower alkyl and Y is halogen, each explained before) (e.g. methylmagnesium bromide, ethylmagnesium bromide, propylmagnesium iodide, etc.), metalated lower alkyl (e.g. methyl lithium, ethyl lithium, etc.) or the like.

The reaction is usually carried out in a solvent such as diethyl ether, tetrahydrofuran or any other solvent which does not adversely affect the reaction.

The reaction temperature is not critical and usually carried out under cooling to heating.

Process 3

The compound (Ic) or a salt thereof can be prepared by reacting the compound (Ia) or a salt thereof with the compound (IV) or a salt thereof.

Suitable salts of the compounds (Ic) and (IV) can be referred to the ones as exemplified for the compound (I).

The present reaction may be carried out in a solvent such as water, phosphate buffer, acetone, chloroform, acetonitrile, nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water. When the compound (IV) is in liquid, it can also be used as a solvent.

The reaction is preferably conducted in the presence of a base, for example, inorganic base such as alkali metal hydride (e.g. sodium hydride, etc.), alkali metal hydroxide, alkali metal carbonate, alkali metal bicarbonate, organic base such as trialkylamine, and the like.

The reaction temperature is not critical, and the reaction is usually carried out at room temperature, under warming or under heating.

The present reaction is preferably carried out in the presence of alkali metal halide [e.g. sodium iodide, potassium iodide, etc.], alkali metal thiocyanate [e.g. sodium thiocyanate, potassium thiocyanate, etc.] or the like.

Process 4

The compound (Id) or a salt thereof can be prepared by subjecting the compound (Ia) or a salt thereof to introduction reaction of acyl which may have one or more suitable substituent(s).

Suitable salt of the compound (Id) can be referred to the ones as exemplified for the compound (I).

This introduction reaction can be carried out by reacting the compound (Ia) or a salt thereof with an acid corresponding to acyl group to be introduced or its reactive derivative at the carboxy group or a salt thereof.

Suitable reactive derivative at the carboxy group may include an acid halide (e.g. acid chloride, etc.), an acid anhydride, an activated amide, an activated ester and the like, which are used conventionally in this field of the art.

This reaction is usually carried out in a conventional solvent such as methylene chloride, chloroform or the like.

The reaction temperature is not critical and the reaction can be carried out under cooling to warming.

Process 5

The compound (If) or a salt thereof can be prepared by reacting the compound (Ie) or a salt thereof with the compound (V) or a salt thereof.

Suitable salts of the compounds (Ie), (If) and (V) can be referred to the ones as exemplified for the compound (I).

This reaction can be carried out according to a similar manner to that as explained in Process 3.

Process 6

The compound (Ig) or a salt thereof can be prepared by subjecting the compound (If) or a salt thereof to reduction.

Suitable salt of the compound (Ig) can be referred to the ones as exemplified for the compound (I).

Suitable reducing agent for this reduction may include lithium aluminum hydride, sodium borohydride and the like.

This reaction is usually carried out in a conventional solvent such as tetrahydrofuran, diethyl ether or the like.

The reaction temperature is not critical and the reaction can be carried out under cooling to heating.

When the compound (I) thus obtained in these processes is a racemic mixture, this mixture can be separated into each stereomer according to a conventional manner.

The processes for preparing the starting compounds (II) and (III) of the present invention are explained in detail in the following.

Step A

The compound (VII) can be prepared by subjecting the compound (VI) or a salt thereof to introduction reaction of the amino protective group.

Suitable salt of the compound (VI) can be referred to the ones as exemplified for the compound (I).

The introduction reaction of the amino protective group in this step can be carried out by reacting the compound (VI) or a salt thereof with a suitable agent for introducing the amino protective group.

Suitable examples of said agent may be ar(lower)alkyl halide which may have aforesaid lower alkoxy such as phenyl(lower)alkyl halide which may have lower alkoxy (e.g. benzyl iodide, 3-methoxybenzyl iodide, benzyl bromide, 4-methoxybenzyl bromide, phenethyl chloride, etc.), diphenyl(lower)alkyl halide (e.g. benzhydryl chloride, etc.), triphenyl(lower)alkyl halide (e.g. trityl bromide, etc.) or the like.

This introduction reaction may be carried out in a suitable solvent such as chloroform, acetonitrile, nitrobenzene, N,N-dimethylformamide or any other solvent which does not adversely affect the reaction.

The reaction temperature is not critical and usually carried out at room temperature, under warming or under heating.

Step B

The compound (II) or a salt thereof can be prepared by reacting the compound (VII) with a lower alkylating agent.

This reaction can be carried out according to a similar manner to that as explained in Process 2.

Step C

The compound (IIIa) or a salt thereof can be prepared by reacting the compound (VI) or a salt thereof with the compound (IV) or a salt thereof.

Suitable salt of the compound (IIIa) can be referred to the ones as exemplified for the compound (I).

This reaction can be carried out according to a similar manner to that as explained in Process 3.

Step D

The compound (IIIb) or a salt thereof can be prepared by subjecting the compound (VI) or a salt thereof to introduction reaction of acyl which may have one or more suitable substituent(s).

Suitable salt of the compound (IIIb) can be referred to the ones as exemplified for the compound (I).

This reaction can be carried out according to a similar manner to that as explained in Process 4.

The object bicyclic amine compound (I) of the present invention is an N-methyl-D-aspartate receptor antagonist and useful as an anticonvulsant and a drug for treatment of the delayed neuronal death induced, for instance, by cerebral ischemia, for example, in case of cardiac arrest in myocardial infarction.

In order to show the usefulness of the object compound (I), we set forth the representative test results in the following.

Test 1: the effect against the convulsion

[I] Test Compound

1-Methyl-1-phenyl-1,2,3,4-tetrahydroisoquinoline hydrochloride (the compound of Example 1)

[II] Test Method

Six- to seven-week-old ICR male mice (5 mice per one group) were used for this experiment.

Test compound dissolved in saline was administered intraperitoneally (dose:100 mg/kg) to each mouse (Test Group).

To the Control Group, only saline was administered. 30 minutes after said administration, N-methyl-D-aspartate (0.32 μg) was injected intracerebroventricularly to each mouse. Then, each mouse was put into a plastic cage and observed for 10 minutes to confirm the occurrence of clonic and tonic seizures.

[III] Test Results

The latency of initial seizure (second) (mean value ± standard error) was shown in the following table.

|  | Latency (second) |
| --- | --- |
| Control group | 5.0 ± 0.7 |
| Test Group | >600** |

**$P < 0.01$

Test 2: the effect against the convulsion

[I] Test Compound (+)-1-Methyl-1-phenyl-1,2,3,4-tetrahydroisoquinoline hydrochloride (the compound of Example 4)

[II] Test Method the same as used in Test 1

[III] Test Results

The latency of initial seizure (second) (mean value ± standard error) was shown in the following table.

|  | Latency (second) |
| --- | --- |
| Control group | 8.4 ± 0.5 |
| Test Group | >600** |

**$P < 0.01$

Test 3: the effect against the delayed neuronal death

[I] Test Compound

1-Methyl-1-phenyl-1,2,3,4-tetrahydroisoquinoline hydrochloride (the compound of Example 1)

[II] Test Method

The effect on ischemia-induced delayed hippocampal neurodegeneration was examined according to the following method:

Eight- to nine-week-old male Wistar rats were used for this experiment.

The vertebral arteries were cauterized within the alar foramina and the common carotid arteries were exposed and looped with surgical suture under anesthesia with thiopental sodium (50 mg/kg i.p.).

Next day, the both carotid arteries were occluded with aneurysm clips for 20 minutes under a slight ether anesthesia. The test compound suspended in 0.5% methylcellulose (dose:100 mg/kg) was administered intraperitoneally 10 minutes prior to ischemic insult (Test Group). To Control Group, only 0.5% methylcellulose was administered.

Seven days after the recirculation, rats were perfusion-fixed with fixative consisting of 1.5% glutamic dialdehyde and 1.0% paraformaldehyde in 0.1M phosphate buffer (pH=7.4). Perfusion was performed at a pressure of 160 cm $H_2O$.

Neuronal cell damage was assessed by counting the number of pyramidal neurons appearing normal in a 1 mm length of CA 1 pyramidal cell layer from each hippocampus in coronal sections (3 ~4 μm) stained by cresyl violet corresponding to 1.9–2.1 mm posterior to the bregma.

[III] Test Results

The number of normal pyramidal neurons in CA 1 (cells/mm) (mean value ± standard error) in each group was shown in the following table.

| group | the number of rats to be used | the number of normal pyramidal neurons in CA 1 |
| --- | --- | --- |
| Normal Group | 8 | 136.0 ± 3.1 |
| Control Group | 7 | 20.9 ± 13.4 |
| Test Group | 4 | 88.3 ± 27.5* |

*P < 0.05: compared with the control group

Test 4: the effect against the delayed neuronal death
[I] Test Compound
(+)-1-Methyl-1-phenyl-1,2,3,4-tetrahydroisoquinoline hydrochloride (the compound of Example 4)
[II] Test Method
The effect on ischemia-induced delayed hippocampal neurodegeneration was examined according to the following method:
Eight- to nine-week-old male Wistar rats were used for this experiment.
The vertebral arteries were cauterized within the alar foramina and the common carotid arteries were exposed and looped with surgical suture under anesthesia with thiopental sodium (50 mg/kg i.p.).
Next day, the both carotid arteries were occluded with aneurysm clips for 20 minutes under a slight ether anesthesia. The test compound suspended in 0.5% methylcellulose (dose:32 mg/kg) was administered intraperitoneally 10 minutes prior to ischemic insult (Test Group). To Control Group, only 0.5% methylcellulose was administered.
Seven days after the recirculation, rats were perfusion-fixed with fixative consisting of 1.5% glutamic dialdehyde and 1.0% paraformaldehyde in 0.1M phosphate buffer (pH=7.4). Perfusion was performed at a pressure of 160 cm $H_2O$.
Neuronal cell damage was assessed by counting the number of pyramidal neurons appearing normal in a 1 mm length of CA 1 pyramidal cell layer from each hippocampus in coronal sections (3~4 μm) stained by cresyl violet corresponding to 1.9-2.1 mm posterior to the bregma.
[III] Test Results
The number of normal pyramidal neurons in CA 1 (cells/mm) (mean value±standard error) in each group was shown in the following table.

| group | the number of rats to be used | the number of normal pyramidal neurons in CA 1 |
| --- | --- | --- |
| Normal Group | 8 | 136.0 ± 3.1 |
| Control Group | 7 | 20.9 ± 13.4 |
| Test Group | 5 | 107.2 ± 16.9** |

**P < 0.01: compared with the control group

Test 5: the effect against the delayed neuronal death
[I] Test Compound
(+)-1-Methyl-1-phenyl-1,2,3,4-tetrahydroisoquinoline hydrochloride (the compound of Example 4)
[II] Test Method
The effect on ischemia-induced delayed hippocampal neurodegeneration was examined according to the following method:
Eight- to ten-week-old male gerbils were used for this experiment.
The both common carotid arteries were exposed under local anesthesia with lidocaine and were occluded with aneurysm clips for 5 minutes. The test compound dissolved in saline (dose:10 mg/kg) was administered intraperitoneally 30 minutes prior to ischemic insult (Test Group). To Control Group, only saline was administered.
Four days after the recirculation, gerbils were perfusion-fixed with fixative consisting of 1.5% glutamic dialdehyde and 1.0% paraformaldehyde in 0.1M phosphate buffer (pH=7.4). Perfusion was performed at a pressure of 160 cm $H_2O$.
Neuronal cell damage was assessed by counting the number of pyramidal neurons appearing normal in a 1 mm length of CA 1 pyramidal cell layer from each hippocampus in coronal sections (3~4 μm) stained by cresyl violet corresponding to 0.5-1 mm posterior to the bregma.
[III] Test Results
The number of normal pyramidal neurons in CA 1 (cells/mm) (mean value±standard error) in each group was shown in the following table.

| group | the number of gerbils to be used | the number of normal pyramidal neurons in CA 1 |
| --- | --- | --- |
| Normal Group | 7 | 201.0 ± 6.5** |
| Control Group | 7 | 3.9 ± 0.9 |
| Test Group | 7 | 91.9 ± 30.2** |

**P < 0.01: compared with the control group

For therapeutic administration, the object compound (I) and pharmaceutically acceptable salts thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc. In general, amounts between 1 mg and about 6,000 mg or even more per day may be administered to a patient. An average single dose of about 50 mg, 100 mg, 250 mg, 500 mg, 1000 mg, 2000 mg of the object compound (I) of the present invention may be used.

The following Preparations and Examples are given for the purpose of illustrating the present invention in more detail.

Preparation 1

A mixture of 1-phenyl-3,4-dihydroisoquinoline (1.0 g) and benzyliodide (1.26 g) in acetonitrile (7 ml) was refluxed for 1 hour. After allowing to cool to room temperature, the reaction mixture was evaporated in vacuo and the residual precipitate was recrystallized from a mixture of diethyl ether (5 ml) and acetonitrile (3 ml). The crystal was collected by filtration, washed with diethyl ether and dried in vacuo to give 1-phenyl-2-benzyl-3,4-dihydroisoquinolinium iodide (1.52 g).
mp: 208°–209° C.
IR (Nujol): 1620, 1600, 1565 cm$^{-1}$,
NMR (DMSO-d$_6$, δ): 3.52 (2 H, t, J=7 Hz), 4.20 (2 H, t, J=7 Hz), 5.10 (2 H, s), 6.96–7.83 (14 H, m).

Preparation 2

The following compound was obtained according to a similar manner to that of Preparation 1.
1-(3-Chlorophenyl)-2-benzyl-3,4-dihydroisoquinolinium iodide
mp: 191°–192° C.
IR (Nujol): 1615, 1595, 1560 cm$^{-1}$
NMR (CDCl$_3$, δ): 3.33 (2 H, t, J=7 Hz), 4.25 (2 H, t, J=7 Hz), 5.12 (2 H, s), 7.06–8.02 (14 H, m).

Preparation 3

To a suspension of 1-phenyl-2-benzyl-3,4-dihydroisoquinolinium iodide (1.0 g) in diethyl ether (10 ml) was added 3 M diethyl ether solution of methylmagnesium bromide (4.5 ml). The mixture was refluxed for 30 minutes with stirring and then poured into saturated ammonium chloride aqueous solution and extracted with ethyl acetate. The separated organic layer was washed with water, sodium chloride aqueous solution and dried over magnesium sulfate and evaporated in vacuo. The residue was crystallized from n-hexane to give 1-methyl-1-phenyl-2-benzyl-1,2,3,4-tetrahydroisoquinoline (0.64 g).
mp: 102°–103° C.
IR (Nujol): 1600, 1580, 1485 cm$^{-1}$
NMR (CDCl$_3$, δ): 1.78 (3 H, s), 2.58–3.10 (4 H, m), 3.22 (1 H, d, J=14 Hz), 3.56 (1 H, d, J=14 Hz), 6.60–7.65 (14 H, m).
Mass: 313 (M+), The following compounds (Preparations 4 and 5) were obtained according to a similar manner to that of Preparation 3.

Preparation 4

1-Ethyl-1-phenyl-2-benzyl-1,2,3,4-tetrahydroisoquinoline
mp: 96°–97° C. (recrystallized from n-hexane).
IR (Nujol): 1600, 1490 cm
NMR (CDCl$_3$, δ): 0.85 (3 H, t, J=7 Hz), 2.12 (1 H, dd, J=7 Hz and 14 Hz), 2.46–3.05 (5 H, m), 3.88 (1 H, d, J=14 Hz), 6.70–7.30 (14 H, m).
Mass: 327 (M+).

Preparation 5

1-Methyl-1-(3-chlorophenyl)-2-benzyl-1,2,3,4-tetrahydroisoquinoline
NMR (CDCl$_3$, δ):1.81 (3 H, s), 2.78–3.75 (6 H, m), 6.62–7.70 (14 H, m).
Mass: 347 (M+).

Example 1

A mixture of 1-methyl-1-phenyl-2-benzyl-1,2,3,4-tetrahydroisoquinoline (0.5 g) and 10% palladium on carbon (50% wet 0.1 g) in acetic acid (15 ml) was hydrogenated under one atmospheric pressure of hydrogen at room temperature for 9 hours. Insoluble material was filtered off and the filtrate was concentrated in vacuo. The residue was dissolved in ethyl acetate and washed with saturated sodium bicarbonate aqueous solution, water, sodium chloride aqueous solution and dried over magnesium sulfate and evaporated in vacuo. The residue was dissolved in ethanol and to the solution was added 7M ethanol solution of hydrogen chloride. The precipitate was collected by filtration, washed with ethanol and diethyl ether and dried in vacuo to give 1-methyl-1-phenyl-1,2,3,4-tetrahydroisoquinoline hydrochloride (0.4 g).
mp: 274°–276° C. (decomp.),
IR (Nujol): 1585, 1490 cm$^{-1}$
NMR (DMSO-d$_6$, δ):2.10 (3 H, s), 2.80–3.50 (4 H, m), 7.05–7.45 (9 H, m), 9.80 (1 H, s), 10.40 (1 H, s)
Mass: 222 (M+ −1)
Elemental Analysis for C$_{16}$H$_{17}$N.HCl;
Calcd.: C 73.98, H 6.98, N 5.45,
Found: C 73.55, H 6.98, N 5.28.

The following compounds (Examples 2 and 3) were obtained according to a similar manner to that of Example 1.

EXAMPLE 2

1-Ethyl-1-phenyl-1,2,3,4-tetrahydroisoquinoline hydrochloride
mp: 288°–290° C.
IR (Nujol): 1580, 1495 cm$^{-1}$.
NMR (DMSO-d$_6$): 0.98 (3 H, t, J=7 Hz), 2.56–3.36 (6 H, m), 7.16–7.36 (9 H, m), 9.65–10.26 (2 H, broad).
Mass: 236 (M+ −1).
Elemental Analysis:
Calcd.: C 74.58, H 7.36, N 5.12,
Found: C 74.57, H 7.42, N 5.08.

EXAMPLE 3

1-Methyl-1-(3-chlorophenyl)-1,2,3,4-tetrahydroisoquinoline hydrochloride
mp: 265°–267° C.
IR (Nujol): 1580, 1495 cm$^{-1}$.
NMR (DMSO-d$_6$): 2.13 (3 H, s), 2.90–3.55 (4 H, m), 7.05–7.50 (8 H, m).
Mass: 257 (M+).
Elemental Analysis:
Calcd.: C 65.32, H 5.82, N 4.76,
Found: C 65.10, H 5.65, N 4.78.

EXAMPLE 4

(1) 1-Methyl-1-phenyl-1,2,3,4-tetrahydroisoquinoline (racemic mixture) (10.2 g) and (+)-di-p-toluoyl-D-tartaric acid (17.65 g) was dissolved in ethanol (270 ml) at about 50° C., then left to stand for 2 days at room temperature. The precipitate was collected by filtration and dissolved in ethanol (180 ml), then left to stand overnight at room temperature. The precipitate was collected by filtration and washed with ethanol, then dried to give (+)-di-p-toluoyl-D-tartaric acid salt of 1-methyl-1-phenyl-1,2,3,4-tetrahydroisoquinoline (4.42 g).

While, the filtrate was evaporated in vacuo and the residue was dissolved in ethyl acetate. The solution was adjusted to pH 8.0 with K$_2$CO$_3$ aqueous solution and organic layer was separated and washed with water and sodium chloride aqueous solution, dried over magnesium sulfate and evaporated in vacuo. The residue (6.0 g) and (−)-di-p-toluoyl-D-tartaric acid monohydrate (10.86 g) was dissolved in ethanol (170 ml), then left to stand overnight at room temperature. The precipitate was collected by filtration and washed with ethanol, then dried to give (−)-di-p-toluoyl-D-tartaric acid salt of 1-methyl-1-phenyl-1,2,3,4-tetrahydroisoquinoline (10.0 g).

(2) (+)-Di-p-toluoyl-D-tartaric acid salt of 1-methyl-1-phenyl-1,2,3,4-tetrahydroisoquinoline (3.0 g) was dissolved in ethyl acetate and the solution was adjusted to pH 8.0 with saturated K$_2$CO$_3$ aqueous solution. The organic layer was separated and washed with water and sodium chloride aqueous solution, dried over magnesium sulfate and evaporated in vacuo. The residue was dissolved in ethanol and added 7M ethanol solution of hydrogen chloride. The precipitate was collected by filtration, washed with ethanol and diethyl ether, then dried to give (+)-1-methyl-1-phenyl-1,2,3,4-tetrahydroisoquinoline hydrochloride (1.20 g).

(−)-1-Methyl-1-phenyl-1,2,3,4-tetrahydroisoquinoline hydrochloride (1.70 g) was obtained according to a similar manner to that of (+) isomer from (−)-di-p-toluoyl-D-tartaric acid salt of 1-methyl-1-phenyl-1,2,3,4-tetrahydroisoquinoline.

Physicochemical Properties of Obtained Compounds (+)-Di-p-toluoyl-D-tartaric acid salt of 1-methyl-1-phenyl-1,2,3,4-tetrahydroisoquinoline
mp: 183°–184° C.,
$[\alpha]_D^{20} = -19.5°$ (C=1, EtOH) (optical rotation was measured after this tartaric acid salt was converted to free form).

(−)-Di-p-toluoyl-D-tartaric acid salt of 1-methyl-1-phenyl-1,2,3,4-tetrahydroisoquinoline
mp: 184°–185° C.
$[\alpha]_D^{20} = +17.9°$ (C=1, EtOH) (optical rotation was measured after this tartaric acid salt was converted to free form).

(+)-1-Methyl-1-phenyl-1,2,3,4-tetrahydroisoquinoline hydrochloride
mp: 302°–303° C.
$[\alpha]_D^{20} = 10.9°$ (C=1, EtOH).
IR (Nujol): 1585, 1500, 1260 cm$^{-1}$.
NMR (DMSO-d$_6$, δ): 2.20 (3 H, s), 2.90–3.70 (4 H, m), 7.15–7.50 (9 H, m).
Mass: 222 (M+−1).

(−)-1-Methyl-1-phenyl-1,2,3,4-tetrahydroisoquinoline hydrochloride
mp: 300°–301° C.
$[\alpha]_D^{20} = -13.30°$ (C=1, EtOH).
IR (Nujol): 1585, 1500, 1260 cm$^{-1}$.
NMR (DMSO-d$_6$, δ): 2.20 (3 H, s), 2.90–3.70 (4 H, m), 7.15–7.50 (9 H, m).
Mass: 222 (M+−1).
Elemental Analysis for C$_{16}$H$_{17}$N.HCl:
Calcd.: C 73.98, H 6.98, N 5.39,
Found: C 74.06, H 6.95, N 5.37.

The following compounds (Preparations 6 to 20) were btained according to a similar manner to that of Preparation 1.

Preparation 6

1-(p-Tolyl)-2-benzyl-3,4-dihydroisoquinolinium iodide
mp:203°–204° C.
IR (Nujol): 1620, 1610, 1560 cm$^{-1}$.
NMR (DMSO-d$_6$, δ): 2.45 (3 H, s), 3.28 (2 H, d, J=7 Hz), 4.15 (2 H, d, J=7 Hz), 5.10 (2 H, s), 7.04–7.86 (13 H, m).

Preparation 7

1-(4-Methoxyphenyl)-2-benzyl-3,4-dihydroisoquinolinium iodide
mp: 76°–78° C.
IR (Nujol): 1600, 1560, 1510 cm$^{-1}$.
NMR (DMSO-d$_6$, δ): 3.24 (2 H, t, J=7 Hz), 3.88 (3 H, s), 4.13 (2 H, t, J=7 Hz), 5.14 (2 H, s), 7.08–7.86 (13 H, m).

Preparation 8

1-(3-Fluorophenyl)-2-benzyl-3,4-dihydroisoquinolinium iodide
mp: 178°–180° C.
IR (Nujol): 1615, 1600, 1580, 1560 cm$^{-1}$.
NMR (DMSO-d$_6$, δ):3.32 (2 H, t, J=7 Hz), 4.17 (2 H, t, J=7 Hz), 5.09 (2 H, s), 7.07–7.88 (13 H, m).

Preparation 9

1-(4-Fluorophenyl)-2-benzyl-3,4-dihydroisoquinolinium iodide
mp: 195°–196° C.
NMR (DMSO-d$_6$, δ):3.40 (2 H, t, J=9 Hz), 4.28 (2 H, t, J=9 Hz), 5.21 (2 H, s), 7.08–8.14 (13 H, m).

Preparation 10

1-(2-Chlorophenyl)-2-benzyl-3,4-dihydroisoquinolinium iodide
mp: 181°–182° C.
IR (Nujol): 1620, 1600, 1565 cm$^{-1}$
NMR (DMSO-d$_6$, δ): 3.256–3.46 (2 H, m), 4.14–4.44 (2 H, m), 5.04 (1 H, d, J=15 Hz), 5.25 (1 H, d, J=15 Hz), 7.04–8.10 (13 H, m)

Preparation 11

1-(4-Chlorophenyl)-2-benzyl-3,4-dihydroisoquinolinium iodide
mp: 188°–189° C.
IR (Nujol): 1615, 1600, 1565, 1480 cm$^{-1}$
NMR (DMSO-d$_6$, δ): 3.32 (2 H, t, J=7 Hz), 4.17 (2 H, t, J=7 Hz), 5.09 (2 H, s), 7.06–7.88 (13 H, m)

Preparation 12

1-Phenyl-2-benzyl-4-methyl-3,4-dihydroisoquinolinium iodide
mp: 195°–197° C.
IR (Nujol): 1610, 1600, 1565, 1480 cm$^{-1}$
NMR (DMSO-d$_6$, δ): 1.13 and 1.16 (total 3 H, each s), 3.35–3.59 (1 H, m), 4.00 (1 H, dd, J=7 Hz and 14 Hz), 4.25 (1 H, dd, J=6 Hz and 14 Hz), 5.03 (1 H, d, J=15 Hz), 5.16 (1 H, d, J=15 Hz), 7.03–7.92 (14 H, m)

Preparation 13

1-Phenyl-2-benzyl-7-methyl-3,4-dihydroisoquinolinium iodide
mp: 211°–212° C.
IR (Nujol): 1620, 1560 cm$^{-1}$
NMR (DMSO-d$_6$, δ): 2.25 (3 H, s), 3.26 (2 H, t, J=7 Hz), 4.15 (2 H, t, J=7 Hz), 5.06 (2 H, s), 6.82 (1 H, s), 7.40–7.81 (12 H, m)

Preparation 14

1-Phenyl-2-benzyl-3-acetoxymethyl-3,4-dihydroisoquinolinium iodide
mp: 176°–177° C.
IR (Nujol): 1740, 1600, 1560 cm$^{-1}$
NMR (DMSO-d$_6$, δ): 1.79 (3 H, s), 3.35 (1 H, s), 3.59–3.71 (1 H, m), 4.37–4.58 (3 H, m), 5.25 (2 H, s), 6.99–7.91 (14 H, m)

Preparation 15

1-Phenyl-2-benzyl-5-chloro-3,4-dihyhroisoquinolinium iodide
mp: 244°–246° C.
IR (Nujol): 1620, 1585, 1560, 1495 cm$^{-1}$
NMR (DMSO-d$_6$, δ): 3.53 (2 H, t, J=8 Hz), 4.22 (2 H, t, J=8 Hz), 5.11 (2 H, s), 7.01–8.02 (13 H, m)

Preparation 16

1-Phenyl-2-benzyl-7-chloro-3,4-dihydroisoquinolinium iodide mp: 236°–237° C.

NMR (DMSO-$d_6$, $\delta$): 3.37 (2 H, t, J=8 Hz), 4.29 (2 H, t, J=8 Hz), 5.16 (2 H, s), 6.98–8.08 (13 H, m)

Preparation 17

1-Phenyl-2-benzyl-6-ethoxycarbonylamino-3,4dihydroisoquinolinium bromide mp: 218°–219° C. (dec.)

IR (Nujol): 3400, 3200, 3140, 1740, 1600 cm$^{-1}$

NMR (DMSO-$d_6$, $\delta$): 1.27 (3 H, t, J=7 Hz), 3.23 (2 H, t, J=7 Hz), 4.09 (2 H, t, J=7 Hz), 4.18 (2 H, t, J=7 Hz), 4.98 (2 H, s), 6.95–7.71 (13 H, m)

Preparation 18

1-Cyclohexyl-2-benzyl-3,4-dihydroisoquinolinium iodide mp: 162°–164° C.

IR (Nujol): 1600, 1560, 1495 cm$^{-1}$

NMR (DMSO-$d_6$, $\delta$): 1.09–2.08 (10 H, m), 3.10 (2 H, t, J=7 Hz), 3.35–3.44 (1 H, m), 3.85 and 4.00 (total 2 H, each t, J=7 Hz), 5.50 (2 H, s), 7.48–8.37 (9 H, m).

Preparation 19

1-(2-Thienyl)-2-(4-methoxybenzyl)-3,4-dihydroisoquinolinium iodide

IR (Film): 1610, 1255 cm$^{-1}$.

NMR (DMSO-$d_6$, $\delta$): 3.20 (2 H, t, J=7 Hz), 3.75 (3 H, s), 4.08 (2 H, t, J=7 Hz), 5.17 (2 H, s), 6.87–8.23 (11 H, m).

Preparation 20

1-Phenyl-2-benzyl-4,5-dihydro-3 H-2-benzazepinium bromide mp: 236°–238° C.

IR (Nujol): 1610, 1595, 1565 cm$^{-1}$.

NMR (DMSO-$d_6$, $\delta$): 1.96 (2 H, t, J=7 Hz), 2.90 (2 H, t, J=7 Hz), 3.89 (2 H, t, J=7 Hz), 5.35 (2 H, s), 6.99–7.84 (14 H, m)

The following compounds (Preparations 21 to 36) were obtained according to a similar manner to that of Preparation 3.

Preparation 21

1-Methyl-1-(p-tolyl)-2-benzyl-1,2,3,4-tetrahydroisoquinoline mp: 139°–140° C.

IR (Nujol): 1600, 1510, 1490 cm$^{-1}$

NMR (CDCl$_3$, $\delta$): 1.78 (3 H, s), 2.60 (3 H, s), 2.60–3.16 (4 H, m), 3.27 (1 H, d, J=14 Hz), 3.57 (1H, d, J=14 Hz), 6.67–7.49 (13 H, m).

Preparation 22

1-Methyl-1-(4-methoxyphenyl)-2-benzyl-1,2,3,4-tetrahydroisoquinoline mp: 113°–114° C.

IR (Nujol): 1600, 1505, 1490 cm$^{-1}$.

NMR (CDCl$_3$, $\delta$): 1.76 (3 H, s), 2.63–3.15 (4 H, m), 3.25 (1 H, d, J=14 Hz), 3.59 (1H, d, J=14 Hz), 3.73 (3 H, s), 6.67–7.52 (13 H, m).

Preparation 23

1-Methyl-1-(3-fluorophenyl)-2-benzyl-1,2,3,4-tetrahydroisoquinoline mp: 83°–85° C.

IR (Nujol): 1605, 1590, 1485 cm$^{-1}$,

Preparation 24

1-Methyl-1-(4-fluorophenyl)-2-benzyl-1,2,3,4-tetrahydroisoquinoline mp: 154°–155° C.

NMR (CDCl$_3$, $\delta$): 1.86 (3 H, s), 2.65–3.06 (4 H, m), 3.33 (1H, d, J=14 Hz), 3.70 (1H, d, J=14 Hz), 6.68–7.78 (13 H, m).

Mass (M/Z): 331 (M$^+$).

Preparation 25

1-Methyl-1-(2-chlorophenyl)-2-benzyl-1,2,3,4-tetrahydroisoquinoline hydrochloride NMR (DMSO-$d_6$, $\delta$): 2.10 (3 H, s), 3.00–4.20 (6 H, m), 7.15–8.00 (13 H, m).

Mass (M/Z): 347 (M$^+$).

Preparation 26

1-Methyl-1-(4-chlorophenyl)-2-benzyl-1,2,3,4-tetrahydroisoquinoline mp: 134°–135° C.

NMR (CDCl$_3$, $\delta$): 1.82 (3 H, s), 2.60–3.05 (4 H, m), 3.28 (1 H, d, J=14 Hz), 3.65 (1 H, d, J=14 Hz), 6.58–7.68 (13 H, m).

Mass (M/Z): 347 (M$^+$).

Preparation 27

1-Methyl-1-phenyl-2-benzyl-4-methyl-1,2,3,4-tetrahydroisoquinoline mp: 125°–126° C.

IR (Nujol): 1600, 1580, 1490 cm$^{-1}$.

NMR (CDCl$_3$, $\delta$): 1.21 and 1.24 (total 3 H, each s), 1.76 (3 H, s), 2.50–3.05 (3 H, m), 3.19 (1 H, d, J=13 Hz), 3.63 (1 H, d, J=13 Hz), 6.63–7.67 (14 H, m).

Preparation 28

1-Methyl-1-phenyl-2-benzyl-7-methyl-1-,2,3,4-tetrahydroisoquinoline mp 94°–95° C., IR (Nujol): 1600, 1490, 1420 cm$^{-1}$.

NMR (DMSO-$d_6$, $\delta$): 1.79 (3 H, s), 2.12 (3 H, s), 2.44–3.12 (4 H, m), 3.17 (2 H, d, J=14 Hz), 3.54 (2 H, d, J=14 Hz), 6.49 (1 H, s), 6.83–7.62 (12 H, m).

Preparation 29

1-Methyl-1-phenyl-2-benzyl-3-hydroxymethyl-1,2,3,4-tetrahydroisoquinoline

IR (Film): 3550, 3400, 1600, 1495, 1450 cm$^{-1}$.

NMR (CDCl$_3$, $\delta$): 1.76 and 1.82 (total 3 H, s), 2.70–4.02 (6 H, m), 6.62–7.52 (14 H, m)

Mass (M/Z): 342 (M$^+$ − 1).

Preparation 30

1-Methyl-1-phenyl-2-benzyl-5-chloro-1,2,3,4-tetrahydroisoquinoline mp: 98°–100° C.

IR (Nujol): 1565, 1490 cm$^{-1}$.

NMR (CDCl$_3$, $\delta$): 1.80 (3 H, s), 2.73–2.95 (4 H, m), 3.26 (1 H, d, J=14 Hz), 3.55 (1H, d, J=14 Hz), 5.58–7.59 (13 H, m).

Preparation 31

1-Methyl-1-phenyl-2-benzyl-7-chloro-1,2,3,4-tetrahydroisoquinoline mp: 96°–97° C.

NMR (CDCl$_3$, δ): 1.85 (3 H, s), 2.60–3.15 (4 H, m), 3.30 (1 H, d, J=14 Hz), 3.62 (1 H, d, J=14 Hz), 6.70–7.72 (13 H, m).

Mass (M/Z): 347 (M+).

Preparation 32

1-Methyl-1-phenyl-2-benzyl-6-ethoxycarbonylamino-1,2,3,4-tetrahydroisoquinoline

IR (Film): 3420, 1720 cm$^{-1}$.

NMR (CDCl$_3$, δ): 12.5 (3 H, t, J=7 Hz), 1.75 (3 H, s), 2.55–3.06 (4 H, m), 3.24 (1 H, d, J=14 Hz), 3.53 (1 H, d, J=14 Hz), 4.18 (2 H, d, J=7 Hz), 6.52–7.62 (14 H, m).

Mass (M/Z): 385 (M+ −15).

Preparation 33

1-Methyl-1-cyclohexyl-2-benzyl-1,2,3,4-tetrahydroisoquinoline

IR (Film): 2940, 1600, 1490, 1450 cm$^{-1}$.

NMR (CDCl$_3$, δ): 1.15–2.10 (14 H, m), 2.56–3.08 (4 H, m), 3.40 (1 H, d, J=15 Hz), 4.22 (1 H, d, J=15 Hz), 7.12–7.54 (9 H, m)

Mass (M/Z): 302 (M+ +1).

Preparation 34

1-Methyl-1-(2-furyl)-2-benzyl-1,2,3,4-tetrahydroisoquinoline

NMR(CDCl$_3$, δ): 1.88 (3 H, s), 2.94 (4 H, s), 3.48 (1 H, d, J=14 Hz), 3.75 (1 H, d, J=14 Hz), 6.44 (2 H, s), 7.05–7.54 (10 H, m)

Mass (M/Z): 303 (M+)

Preparation 35

1-Methyl-1-(2-thienyl)-2-(4-methoxybenzyl)-1,2,3,4-tetrahydroisoquinoline mp: 80–82° C.

IR (Nujol): 1610, 1240, 1035, 700 cm$^{-1}$

NMR (CDCl$_3$, δ): 1.81 (3 H, s), 2.5–3.2 (4 H, m), 3.30 (1 H, d, J=14 Hz), 3.68 (1 H, d, J=14 Hz), 3.72 (3 H, s), 6.7–7.4 (11 H, m)

Preparation 36

1-Methyl-1-phenyl-2-benzyl-2,3,4,5-tetrahydro-1H-2-benzazepine mp: 134°–135° C.

IR (Nujol): 1600, 1485 cm$^{-1}$

NMR (CDCl$_3$, δ): 1.11–1.29 (1H, m), 1.73–1.79 (1 H, m), 1.89 (3 H, s), 2.56–2.84 (3 H, m), 3.35–3.46 (1 H, m), 3.35 (1 H, d, J=7 Hz), 3.80 (1 H, d, J=7 Hz), 7.15–7.44 (14 H, m)

Mass (M/Z): 312 (M+ −15)

Preparation 37

1-Methyl-1-(3-thienyl)-2-(4-methoxybenzyl)-1,2,3,4-tetrahydroisoquinoline was prepared by reacting 1-(3-thienyl)-3,4-dihydroisoquinoline with 4-methoxybenzyl bromide according to a similar manner to that of Preparation 1, and then by reacting the obtained 1-(3-thienyl)-2-(4-methoxybenzyl)-3,4-dihydroisoquinolinium bromide with 3M diethyl ether solution of methylmagnesium bromide according to a similar manner to that of Preparation 3.

IR (Film): 1610, 1040 cm$^{-1}$.

NMR (CDCl$_3$, δ): 1.78 (3 H, s), 2.8–3.1 (4 H, m), 3.20 (1H, d, J=13.5 Hz), 3.28 (1 H, d, J=13.5 Hz), 3.78 (3 H, s), 6.9–7.2 (11 H, m).

Preparation 38

The mixture of 1-phenyl-3,4-dihydroisoquinoline (292.0 g) and benzyl bromide (176 ml) in acetonitrile (3 l) was refluxed for 1 hour. After cooling the mixture to room temperature, the solvent was evaporated in vacuo. The residue was triturated with diethyl ether (1 l) to give 1-phenyl-2-benzyl-3,4-dihydroisoquinolinium bromide (471.2 g).

mp: 181°–183° C.

IR (nujol): 1620, 1600 cm$^{-1}$.

NMR (DMSO-d$_6$, δ): 3.24 (2 H, t, J=5 Hz), 4.14 (2 H, t, J=5 Hz), 5.02 (2 H, s), 6.88–7.86 (14 H, m).

Preparation 39

To a suspension of 1-phenyl-2-benzyl-3,4-dihydroisoquinolinium bromide (353.1 g) in tetrahydrofuran (3.5 l) was added 2.0M tetrahydrofuran solution of methylmagnesium bromide (700 ml) for 1.5 hours with stirring at room temperature. After additional stirring for 1.5 hours, the mixture was poured into a solution of ammonium chloride (300 g) in water (650 ml) under ice cooling. After separation, the aqueous layer was extracted with ethyl acetate (3.5 l). The combined organic layers were washed with water (1 l), sodium chloride aqueous solution (1 l) and dried over magnesium sulfate (125 g) and evaporated in vacuo. The residue was crystallized from ethanol (500 ml) to give 1-methyl-1-phenyl-2-benzyl-1,2,3,4-tetrahydroisoquinoline (254.0 g).

mp: 102°–103° C.

IR (Nujol): 1600, 1580, 1485 cm$^{-1}$

NMR (CDCl$_3$, δ): 1.78 (3 H, s), 2.58–3.10 (4 H, m), 3.22 (1 H, d, J=14 Hz), 3.56 (1 H, d, J=14 Hz), 6.60–7.65 (14 H, m)

Mass: 313 (M+)

The following compounds (Preparations 40 to 42) were obtained according to a similar manner to that of Preparation 1.

Preparation 40

1-Phenyl-2-ethyl-3,4-dihydroisoquinolinium iodide mp: 165°–166° C. (dec.)

IR (Nujol): 1620, 1600, 1560 cm$^{-1}$

NMR (DMSO-d$_6$, δ): 1.35 (3 H, t, J=7 Hz), 3.35–3.45 (2 H, m), 3.78 (2 H, t, J=7 Hz)

Preparation 41

1-(2-Thienyl)-2-methyl-3,4-dihydroisoquinolinium iodide mp: 180°–181° C. (dec.)

IR (Nujol): 1590, 720 cm$^{-1}$

NMR (DMSO-d$_6$, δ): 3.25–3.6 (2 H, m), 3.75 (3 H, s), 4.2–4.55 (2 H, m), 7.2–8.0 (7 H, m)

Preparation 42

1-(2-Thienyl)-2-ethyl-3,4-dihydroisoquinolinium iodide mp: 194°–195° C.

IR (Nujol): 1600, 800, 740 cm$^{-1}$.

NMR (DMSO-d$_6$): 1.43 (3 H, t, J=8 Hz), 3.2–3.5 (2 H, m), 3.7–4.2 (2 H, m), 4.25 (2 H, t, J=8 Hz),

The following compounds (Examples 5 to 18) were obtained according to a similar manner to that of Example 1.

Example 5

1-Methyl-1-(p-tolyl)-1,2,3,4-tetrahydroisoquinoline hydrochloride mp: 294°–295° C.

IR (Nujol): 1575, 1510, 1490 cm$^{-1}$.

NMR (DMSO-d$_6$, δ): 2.12 (3 H, s), 2.32 (3 H, s), 2.80–3.85 (4 H, m), 7.12–7.40 (8 H, m), 10.00 (1 H, s), 10.55 (1 H, s).

Mass (M+/Z): 236 (M+ −1).

Example 6

1-Methyl-1-(4-methoxyphenyl)-1,2,3,4-tetrahydroisoquinoline hydrochloride
mp: 251°–253° C.
IR (Nujol): 1610, 1585, 1535 cm$^{-1}$.
NMR (DMSO-d$_6$, δ): 2.15 (3 H, s), 2.85–3.50 (4 H, m), 3.80 (3 H, s), 6.90–7.50 (8 H, m)
Mass (M/Z): 252 (M+ −1).
Elemental analysis for C$_{17}$H$_{19}$NO·HCl.
Calcd. : C 70.46, H 6.96, N 4.83.
Found : C 70.06, H 7.00, N 4.80.

Example 7

1-Methyl-1-(3-fluorophenyl)-1,2,3,4-tetrahydroisoquinoline hydrochloride
mp : 285°–287° C. Nujol) : 1605, 1585, 1490 cm$^{-1}$.
NMR (DMSO-d$_6$, δ): 2.06 (3 H, s), 2.80–3.40 (4 H, m), 6.95–7.48 (8 H, m), 10.00 (1 H, broad), 10.42 (1 H, broad).
Mass (M/Z): 240 (M+ −1).
Elemental Analysis for C$_{16}$H$_{16}$FN·HCl: Calcd. : C 69.19, H 6.17, N 5.04. Found: C 68.79, H 6.45, N 4.97.

Example 8

1-Methyl-1-(4-fluorophenyl)-1,2,3,4-tetrahydroisoquinoline hydrochloride
mp: 254°–256° C.
IR (Nujol): 1600, 1585, 1510, 1490 cm$^{-1}$.
NMR (DMSO-d$_6$, δ): 2.18 (3 H, s), 2.70–3.55 (4 H, m), 7.10–7.60 (8 H, m), 9.80–10.80 (2 H, broad).
Mass (M/Z): 240 (M+ −1).
Elemental Analysis for C$_{16}$H$_{16}$FN·HCl,
Calcd. : C 69.19, H 6.17, N 5.04;
Found: C 68.84, H 6.09, N 4.96.

Example 9

1-Methyl-1-(2-chlorophenyl)-1,2,3,4-tetrahydroisoquinoline hydrochloride
mp: 264°–265° C. (dec.)
IR (Nujol): 1580, 1490, 1435 cm$^{-1}$.
NMR (DMSO-d$_6$, δ): 2.26 (3 H, s), 3.00–3.70 (4 H, m), 6.58–8.10 (8 H, m).
Mass (M/Z): 257 (M+).
Elemental Analysis for C$_{16}$H$_{16}$ClN·HCl·½H$_2$O:
Calcd.: C 63.38, H 5.98, N 4.62,
Found: C 63.78, H 6.14, N 4.37.

Example 10

1-Methyl-1-(4-chlorophenyl)-1,2,3,4-tetrahydroisoquinoline hydrochloride mp: 286°–287° C. (dec.).
IR (Nujol): 1580, 1490, 1420, 1400 cm$^{-1}$.
NMR (DMSO-d$_6$, δ): 2.12 (3 H, s), 2.80–3.50 (4 H, m), 7.00–7.53 (8 H, m), 10.12 (1 H, broad), 10.55 (1 H, broad).
Mass (M/Z): 256 (M+ −1)

Example 11

1-Methyl-1-phenyl-4-methyl-1,2,3,4-tetrahydroisoquinoline hydrochloride
mp: 245° C. (dec.).
IR (Nujol): 1585, 1490 cm$^{-1}$.
NMR (DMSO-d$_6$, δ): 1.25 (3 H, d, J=7 Hz), 2.22 (3 H, s), 3.20–3.78 (3 H, m), 7.26–7.62 (9 H, m), 10.00–10.70 (2 H, broad).
Mass (M/Z): 236 (M+ −1).
Elemental Analysis for C$_{17}$H$_{19}$N·HCl.
Calcd.: C 74.58, H 7.36, N 5.12.
Found: C 74.37, H 7.12, N 5.15.

Example 12

1-Methyl-1-phenyl-7-methyl-1,2,3,4-tetrahydroisoquinoline hydrochloride
mp: 304°–305° C. (dec.).
IR (Nujol): 1590, 1500 cm$^{-1}$.
NMR (DMSO-d$_6$, δ): 2.20 (3 H, s), 2.32 (3 H, s), 3.05–3.35 (4 H, m), 7.02 (1 H, s), 7.24 (2 H, s),
Mass (M/Z): 236 (M+ −1).
Elemental Analysis for C$_{17}$H$_{19}$N·HCl·¼H$_2$O:
Calcd.: C 73.37, H 7.42, N 5.03;
Found: C 73.53, H 7.47, N 5.00.

Example 13

1-Methyl-1-phenyl-3-hydroxymethyl-1,2,3,4-tetrahydroisoquinoline
mp: 125°–127° C.
IR (Nujol): 3250, 1595, 1585, 1490 cm$^{-1}$.
NMR (CDCl$_3$, δ): 1.85 (3 H, s), 2.58–3.00 (3 H, m), 3.30–3.98 (2 H, m), 7.12–7.22 (9 H, m).
Mass (M/Z): 252 (M+ −1).
Elemental Analysis for C$_{17}$H$_{19}$NO:
Calcd.: C 80.57, H 7.56, N 5.53.
Found: C 80.21, H 7.35, N 5.41.

Example 14

1-Methyl-1-phenyl-5-chloro-1,2,3,4-tetrahydroisoquinoline hydrochloride
mp: 315° C. (dec.)
IR (Nujol): 1575, 1490 cm$^{-1}$.
NMR (DMSO-d$_6$, δ): 2.16 (3 H, s), 2.90–3.40 (4 H, m), 7.05–7.56 (8 H, m).
Elemental Analysis for C$_{16}$H$_{16}$ClN·HCl:
Calcd. : C 65.32, H 5.82, N 4.76 ;
Found: C 65.18, H 5.80, N 4.56 .

Example 15

1-Methyl-1-phenyl-7-chloro-1,2,3,4-tetrahydroisoquinoline hydrochloride
mp : 319°–320° C. (dec.).
IR (Nujol): 1585, 1480 cm$^{-1}$.
NMR (DMSO-d$_6$, δ): 2.24 (3 H, s), 3.10–3.40 (4 H, m), 7.38–7.62 (8 H, m).
Elemental Analysis for C$_{16}$H$_{16}$ClN·HCl·⅓H$_2$O:
Calcd.: C 64.01, H 5.93, N 4.67;
Found: C 64.05, H 5.99, N 4.50.

Example 16

1-Methyl-1-phenyl-6-ethoxycarbonylamino-1,2,3,4-tetrahydroisoquinoline hydrochloride
mp: 260°–261° C. (dec.).
IR (Nujol): 3260, 1730, 1600, 1585 cm$^{-1}$.
NMR (DMSO-d$_6$, δ): 1.35 (3 H, t, J=7 Hz), 2.28 (3 H, s), 2.95–3.40 (4 H, m), 4.25 (2 H, q, J=7 Hz), 7.10–7.65 (8 H, m), 9.82 (1 H, s).
Mass (M/Z): 311 (M+ +1).

Example 17

1-Methyl-1-cyclohexyl-1,2,3,4-tetrahydroisoquinoline hydrochloride
mp: 280°–281° C.
IR (Nujol): 1590, 1495, 1415 cm$^{-1}$.
NMR (DMSO-d$_6$, δ): 1.00–2.35 (14 H, m), 2.80–3.55 (4 H, m), 7.22–7.40 (4 H, m).
Mass (M/Z): 228 (M+ −1).

Example 18

1-Methyl-1-(2-furyl)-1,2,3,4-tetrahydroisoquinoline hydrochloride mp: 223°–225° C.
IR (Nujol): 1580, 1485, 1425 cm$^{-1}$.
NMR (DMSO-d$_6$, δ): 2.12 (3 H, s), 3.16–3.58 (4 H, m), 6.40–6.58 (2 H, m), 7.18–7.36 (4 H, m), 7.75 (1 H, broad), 10.08 (1 H, broad), 10.82 (1 H, broad).
Mass (M/Z): 212 (M$^+$ − 1).
Elemental Analysis for C$_{14}$H$_{15}$NO·HCl:
Calcd.: C 67.33, H 6.46, N 5.61;
Found: C 66.60, H 6.27, N 5.45.

Example 19

To a solution of ceric ammonium nitrate (7 g) in a mixture of acetonitrile (30 ml) and water (15 ml) was added 1-methyl-1-(2-thienyl)-2-(4-methoxybenzyl)-1,2 3,4-tetrahydroisoquinoline (1.5 g). After stirring for 1.5 hours at room temperature, the mixture was poured into a mixture of n-hexane (50 ml) and water (50 ml) with stirring. The separated aqueous layer was adjusted to pH 10 with saturated potassium carbonate aqueous solution and extracted with ethyl acetate (50 ml×2). The organic layer was washed with sodium chloride aqueous solution, dried over magnesium sulfate and extracted in vacuo. The residue was recrystallized from 6N-hydrogen chloride ethanol solution (1 ml) and diethyl ether (10 ml) to give 1-methyl-1-(2-thienyl)-1,2,3,4-tetrahydroisoquinoline hydrochloride (0.51 g).

mp: 264°–265° C. (dec.).
IR (Nujol): 1580, 1260 cm$^{-1}$.
NMR (DMSO-d$_6$, δ): 2.18 (3H, s), 2.8–3.5 (4 H, m), 6.9–7.6 (7 H, m), 9.8–10.7 (2 H, broad).
Elemental Analysis for C$_{14}$H$_{15}$NS·HCl:
Calcd.: C 63.26, H 6.07, N 5.27,
Found: C 62.68, H 5.96, N 5.07.

Example 20

1-Methyl-1-(3-thienyl)-1,2,3,4-tetrahydroisoquinoline hydrochloride was obtained according to a similar manner to that of Example 19.

mp: 280°–281° C. (dec.).
IR (Nujol): 1580, 1165, 800 cm$^{-1}$.
NMR (DMSO-d$_6$, δ): 2.12 (3 H, s), 2.8–3.3 (4 H, m), 7.1–7.3 (6 H, m), 7.5–7.7 (1 H, m), 10.05 (1 H, broad), 10.33 (1 H, broad).
Elemental Analysis for C$_{14}$H$_{15}$NS·HCl:
Calcd.: C 63.26, H 6.06, N 5.26,
Found: C 63.06, H 5.64, N 5.08.

Example 21

1-Methyl-1-(2-thienyl)-1,2,3,4-tetrahydroisoquinoline hydrochloride was subjected to optical resolution according to a similar manner to that of Example 4 to give the following pair of enantiomers.

i) (+)-1-Methyl-1-(2-thienyl)-1,2,3,4-tetrahydroisoquinoline hydrochloride
mp: 292°–293° C.,
[α]$_D^{25}$ = +8.9° (c=1, MeOH).
IR (Nujol): 2700, 1580, 1260 cm$^{-1}$.
NMR (DMSO-d$_6$, δ): 2.22 (3 H, s), 2.8–3.4 (4 H, m), 7.0–7.7 (7 H, m), 9.8–10.9 (2 H, broad).

ii) (−)-1-Methyl-1-(2-thienyl)-1,2,3,4-tetrahydroisoquinoline hydrochloride
mp: 289°–290° C. (dec.),
[α]$_D^{25}$ = −10.00° (c=1, EtOH).
IR (Nujol): 2700, 1580, 1260 cm$^{-1}$.

NMR (DMSO-d$_6$, δ): 2.27 (3 H, s), 3.0–3.4 (4 H, m), 7.0–7.7 (7 H, m), 9.8–10.9 (2 H, broad).
Elemental Analysis for C$_{14}$H$_{16}$ClNS·¼H$_2$O:
Calcd.: C 62.21, H 6.15, N 5.18,
Found: C 62.58, H 6.26, N 5.13.

Example 22

To a suspension of 1-phenyl-2-methyl-3,4-dihydroisoquinolinium iodide (1.0 g) in tetrahydrofuran (15 ml) was added 3M diethyl ether solution of methyl magnesium bromide (1.9 ml) with stirring at room temperature. After stirring for 30 minutes, the mixture was poured into saturated ammonium chloride aqueous solution and ethyl acetate. The organic layer was washed with water, sodium chloride aqueous solution and dried over magnesium sulfate, and evaporated in vacuo. The residue was recrystallized from n-hexane to give 1,2-dimethyl-1-phenyl-1,2,3,4-tetrahydroisoquinoline (0.6 g).

mp : 39°–40° C.,
IR (Nujol): 1600, 1590, 1490 cm$^{-1}$,
NMR (CDCl$_3$, δ): 1.70 (3 H, s), 2.15 (3 H, s), 2.68–3.25 (4 H, m), 6.62–7.50 (9 H, m).
Mass (M/Z): 237 (M$^+$).

The following compounds (Examples 23 to 25) were obtained according to a similar manner to that of Example 22.

Example 23

1-Methyl-1-phenyl-2-ethyl-1,2,3,4-tetrahydroisoquinoline hydrochloride mp: 193°–194° C.
IR (Nujol): 1490, 1420, 1400 cm$^{-1}$,
NMR (DMSO-d$_6$, δ): 1.24–1.34 (3 H, m), 2.02–2.35 (total 3 H, s), 2.90–3.70 (6 H, m), 6.62–7.64 (9 H, m), 10.50–10.80 (1 H, broad), 11.30–11.60 (1 H, broad).
Mass (M/Z): 251 (M$^+$).
Elemental Analysis for C$_{18}$H$_{21}$N·HCl·¼H$_2$O:
Calcd.: C 73.95, H 7.75, N 4.79,
Found: C 74.21, H 7.44, N 4.80.

Example 24

1,2-Dimethyl-1-(2-thienyl)-1,2,3,4-tetrahydroisoquinoline hydrochloride mp: 220°–222° C.
IR (Nujol): 2320, 1260, 725 cm$^{-1}$
NMR (D$_2$O, δ): 2.27 (3 H, s), 2.89 (3 H, s), 3.2–3.8 (4 H, m), 7.0–7.7 (7 H, m)
Elemental Analysis for C$_{15}$H$_{18}$ClNS:
Calcd.: C 64.38, H 6.48, N 5.01,
Found: C 63.83, H 6.44, N 4.94.

Example 25

1-Methyl-1-(2-thienyl)-2-ethyl-1,2,3,4-tetrahydroisoquinoline hydrochloride mp: 198°–200° C.
IR (Nujol): 1175, 740 cm$^{-1}$.
NMR (DMSO-d$_6$, δ): 1.34 (3 H, t, J=7.5 Hz), 2.22 (3 H, s), 3.0–3.9 (6 H, m), 6.9–7.7 (7 H, m).

Example 26

A solution of 1-phenyl-3,4-dihydroisoquinoline (1.0 g) and allyl bromide (0.44 ml) in acetonitrile (10 ml) was refluxed for 2 hours. After cooling it to room temperature, the solvent was evaporated in vacuo and then the residue was stirred in diethyl ether (15 ml) at room temperature. To the mixture was added 3M diethyl ether solution of methylmagnesium bromide (2.0 ml).

After 1 hour, the mixture was poured into aqueous ammonium chloride solution. The organic layer was washed with water, sodium chloride aqueous solution and dried over magnesium sulfate, and evaporated in vacuo to give 1-methyl-1-phenyl-2-allyl-1,2,3,4-tetrahydroisoquinoline (0.7 g).

IR (Film): 1640, 1600, 1490, 1450 cm$^{-1}$.

NMR (CDCl$_3$, δ): 1.69 (3 H, s), 2.70–3.15 (6 H, m), 4.98–5.19 (2 H, m), 5.54–5.78 (1 H, m), 6.64–7.54 (9 H, m).

Mass (M/Z): 263 (M+).

Example 27

1-Methyl-1-phenyl-2-phenethyl-1,2,3,4-tetrahydroisoquinoline hydrochloride was prepared by reacting 1-phenyl-3,4-dihydroisoquinoline with phenethyl bromide, then 3M diethyl ether solution of methylmagnesium bromide according to a similar manner to that of Example 26, and then converting the resultant compound to its hydrochloride according to a conventional manner.

mp: 255°–256° C.

IR (Nujol): 1600, 1580, 1490, 1420 cm$^{-1}$.

NMR (DMSO-d$_6$, δ): 2.15 and 2.48 (total 3 H, s), 3.05–3.50 (4 H, m), 3.55–4.20 (4 H, m), 7.10–8.00 (14 H, m).

Mass (M/Z): 325 (M+ −15).

Elemental Analysis for C$_{24}$H$_{25}$N·HCl·0.1H$_2$O:
Calcd.: C 78.81, H 7.22, N 3.82,
Found: C 78.77, H 7.30, N 3.79.

Example 28

To a solution of (+)-1-methyl-1-phenyl-1,2,3,4-tetrahydroisoquinoline (1.0 g) in N,N-dimethylformamide (10 ml) was added sodium hydride (0.19 g) in ice-bath with stirring. After stirring for 30 minutes at room temperature, to the mixture was added methyl iodide (0.31 ml). And after stirring for an hour at room temperature, the mixture was poured into ice-water and extracted with ethyl acetate. The organic layer was washed with water, sodium chloride aqueous solution, dried over magnesium sulfate and evaporated in vacuo to give (+)-1,2-dimethyl-1-phenyl-1,2,3,4-tetrahydroisoquinoline (0.6 g).

[α]$_D^{20}$ = +105.6° (c=1.3 EtOH).

IR (Film): 1600, 1585, 1495, 1450 cm$^{-1}$.

NMR (CDCl$_3$, δ): 1.64 (3 H, s), 2.11 (3 H, s), 2.72–3.30 (4 H, m), 6.62–7.44 (9 H, m).

Mass (M/Z): 237 (M+).

Example 29

To a solution of 1-methyl-1-phenyl-1,2,3,4-tetrahydroisoquinoline (1.0 g) in methylene chloride (10 ml) was added chloroacetic anhydride (2.9 g) and the mixture was stirred overnight at room temperature. The solvent was evaporated in vacuo. The residue was poured into saturated aqueous solution of sodium bicarbonate and extracted with ethyl acetate. The organic layer was washed with water, sodium chloride aqueous solution and dried over magnesium sulfate, evaporated in vacuo. The resultant precipitate was recrystallized from diethyl ether and dried in vacuo to give 1-methyl-1-phenyl-2-(2-chloroacetyl)-1,2,3,4-tetrahydroisoquinoline (0.77 g).

mp: 150°–152° C.

IR (Nujol): 1665, 1640 cm$^{-1}$.

NMR (CDCl$_3$, δ): 2.03 (3 H, s), 3.04 (1 H, d, J=11 Hz), 3.06 (1 H, d, J=11 Hz), 3.75–4.12 (4 H, m), 6.62–7.34 (9 H, m).

Mass (M/Z): 299 (M+).

Example 30

To a solution of 1-methyl-1-phenyl-2-(2-chloroacetyl)-1,2,3,4-tetrahydroisoquinoline (1.0 g) in methylene chloride (10 ml) was added piperidine (0.82 ml) under ice-cooling, and the mixture was stirred for 3 hours at room temperature. The reaction mixture was poured into water and extracted with methylene chloride. The organic layer was washed with saturated aqueous solution of sodium bicarbonate, sodium chloride aqueous solution and dried over magnesium sulfate, evaporated in vacuo. The residue was dissolved in ethanol (5 ml) and to the solution was added 6M ethanol solution of hydrogen chloride (1 ml). The mixture was evaporated in vacuo and the residue was recrystallized from isopropyl alcohol and diisopropyl ether. The crystal was washed with diethyl ether and dried in vacuo to give 1-methyl-1-phenyl-2-(2-piperidino-acetyl)-1,2,3,4-tetrahydroisoquinoline hydrochloride (0.4 g).

mp: 146°–147° C. (dec.).

IR (Nujol): 3340, 1660 cm$^{-1}$.

NMR (DMSO-d$_6$, δ): 1.60–1.72 (6 H, m), 2.05 (3 H, s), 2.95–3.34 (4 H, m), 3.64–3.84 (2 H, m), 4.34–4.57 (2 H, m), 6.73–7.38 (9 H, m), 9.30 (1 H, s).

Mass (M/Z): 348 (M+),

Elemental Analysis for C$_{23}$H$_{28}$N$_2$O (free):
Calcd.: C 79.27, H 8.09, N 8.03,
Found: C 79.20, H 7.37, N 8.01.

Example 31

A solution of 1-methyl-1-phenyl-2-(2-piperidinoacetyl)-1,2,3,4-tetrahydroisoquinoline (1.0 g) in tetrahydrofuran (5 ml) was dropped into a suspension of lithium aluminum hydride (0.16 g) in tetrahydrofuran (15 ml) over a period of 30 minutes under refluxing. The reaction mixture was heated under refluxing for an additional 1 hour. After cooling it in an ice-bath, to the reaction mixture was added ethyl acetate (5 ml), water (1 ml), 4N aqueous solution of sodium hydroxide (1 ml) and magnesium sulfate (2 g), then the mixture was filtrated and evaporated in vacuo. The residue was dissolved in ethanol (10 ml) and to the solution was added 6M ethanol solution of hydrogen chloride (2 ml). The precipitate was collected by filtration and washed with diethyl ether, and dried in vacuo to give 1-methyl-1-phenyl-2-(2-piperidinoethyl)-1,2,3,4-tetrahydroisoquinoline dihydrochloride (0.4 g).

mp: 130° C. (dec.)

IR (Nujol): 3380, 1590 cm$^{-1}$

NMR (DMSO-d$_6$+D$_2$O, δ): 1.40–1.70 (6 H, broad), 2.13 (3 H, s), 2.68–2.86 (4 H, broad), 3.22–3.63 (8 H, broad), 6.70–7.56 (9 H, m).

Mass (M/Z): 334 (M+).

Elemental Analysis for C$_{23}$H$_{30}$N$_2$·2HCl:
Calcd.: C 67.80, H 7.91, N 6.87, Cl 17.40,
Found: C 67.44, H 7.71, N 6.46, Cl 17.32.

Example 32

1-Methyl-1-phenyl-2,3,4,5-tetrahydro-1H-2-benzazepine hydrochloride was obtained according to a similar manner to that of Example 1.

mp: 275°–277° C.

IR (Nujol): 1580, 1480 cm$^{-1}$.

NMR (DMSO-d$_6$, δ): 1.58–1.85 (2 H, m), 2.12 (3 H, s), 2.38–3.25 (4 H, m), 7.20–7.55 (9 H, m).

Mass (M/Z): 236 (M$^+$ −1).

Elemental Analysis for C$_{17}$H$_{19}$N·HCl·½H$_2$O:
Calcd.: C 73.60, H 7.41, N 5.04,
Found: C 74.05, H 7.82, N 5.05.

The following compounds (Examples 33 to 37) were obtained according to a similar manner to that of Example 28.

Example 33

1-Methyl-1-phenyl-2-ethyl-1,2,3,4-tetrahydroisoquinoline hydrochloride
IR (Nujol): 1490, 1420, 1400 cm$^{-1}$.

Example 34

1,2-Dimethyl-1-(2-thienyl)-1,2,3,4-tetrahydroisoquinoline hydrochloride
IR (Nujol): 2320, 1260, 725 cm$^{-1}$.

Example 35

1-Methyl-1-(2-thienyl)-2-ethyl-1,2,3,4-tetrahydroisoquinoline hydrochloride
IR (Nujol): 1175, 740 cm$^{-1}$.

Example 36

1-Methyl-1-phenyl-2-allyl-1,2,3,4-tetrahydroisoquinoline
IR (Film): 1640, 1600, 1490, 1450 cm$^{-1}$.

Example 37

1-Methyl-1-phenyl-2-phenethyl-1,2,3,4-tetrahydroisoquinoline hydrochloride
IR (Nujol): 1600, 1580, 1490, 1420 cm$^{-1}$.

The following compounds (Examples 38 and 39) were obtained according to a similar manner to that of Example 22.

Example 38

1-Methyl-1-phenyl-2-(2-piperidinoacetyl)-1,2,3,4-tetrahydroisoquinoline hydrochloride
IR (Nujol): 3340, 1660 cm$^{-1}$.

Example 39

1-Methyl-1-phenyl-2-(2-piperidinoethyl)-1,2,3,4-tetrahydroisoquinoline dihydrochloride
IR (Nujol): 3380, 1590 cm$^{-1}$.

Example 40

1-Methyl-1-phenyl-2-(2-piperidinoacetyl)-1,2,3,4-tetrahydroisoquinoline hydrochloride was obtained according to a similar manner to that of Example 29.
IR (Nujol): 3340, 1660 cm$^{-1}$.

Example 41

1-Methyl-1-phenyl-2-(2-piperidinoethyl)-1,2,3,4-tetrahydroisoquinoline dihydrochloride was obtained according to a similar manner to that of Example 28.
IR (Nujol): 3380, 1590 cm$^{-1}$.

What we claim is:

1. A bicyclic amine compound of the formula:

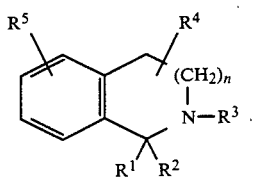

wherein
R$^1$ is lower alkyl,
R$^2$ is aryl which may have one or more suitable substituent(s), cyclo(lower)alkyl or heterocyclic group,
R$^3$ is hydrogen, lower alkyl which may have one or more suitable substituent(s), lower alkenyl, or acyl which may have one or more suitable substituent(s),
R$^4$ is hydrogen, lower alkyl, or hydroxy(lower)alkyl,
R$^5$ is hydrogen, lower alkyl, halogen, or protected amino, and
n is an integer of 1 or 2, with the proviso that when R$^3$ is lower alkyl which may have one or more suitable substituent(s), R$^2$ is cyclo(lower)alkyl or heterocyclic group, or a pharmaceutically acceptable salt thereof.

2. A compound of claim 1, wherein
R$^2$ is aryl which may have 1 to 3 suitable substituent(s) selected from a group consisting of lower alkyl, lower alkoxy and halogen; cyclo(lower)alkyl or unsaturated 5- or 6-membered heterocyclic group having 1 to 3 oxygen or sulfur atom(s),
R$^3$ is hydrogen, lower alkyl which may have 1 to 3 suitable substituent(s) selected from a group consisting of aryl and cyclic amino; lower alkenyl or acyl which may have 6b 1 to 3 suitable substituent(s) selected from a group consisting of halogen and cyclic amino, with the proviso that when R$^3$ is lower alkyl which may have 1 to 3 suitable substituent(s) selected from a group consisting of aryl and cyclic amino, R$^2$ is cyclo(lower)alkyl or unsaturated 5- or 6-membered hetero-cyclic group having 1 to 3 oxygen or sulfur atom(s).

3. A compound of claim 2, wherein
R$^2$ is phenyl which may have 1 to 3 suitable substituent(s) selected from a group consisting of lower alkyl, lower alkoxy and halogen, cyclo(lower)alkyl or unsaturated 5-membered heterocyclic group having 1 to 2 oxygen or sulfur atoms(s),
R$^3$ is hydrogen, lower alkyl which may have 1 to 3 suitable substituent(s) selected from a group consisting of phenyl and 6-membered cyclic amino; lower alkenyl or lower alkanoyl which may have 6b 1 to 3 suitable substituent(s) selected from a group consisting of halogen and 6-membered cyclic amino, with the proviso that when R$^3$ is lower alkyl which may have 1 to 3 suitable substituent(s) selected from a group consisting of phenyl and 6-membered cyclic amino, R$^2$ is cyclo(lower)alkyl or unsaturated 5-membered heterocyclic group having 1 to 2 oxygen or sulfur atom(s).

4. A compound of claim 3, wherein
R$^2$ is phenyl, phenyl having lower alkyl, phenyl having lower alkoxy, phenyl having halogen, cyclo(lower)alkyl, furyl or thienyl,
R$^3$ is hydrogen, lower alkyl, lower alkyl having phenyl, lower alkyl having piperidino, lower alkenyl, lower alkanaoyl having halogen or lower alkanoyl having piperidino, and $R^5$ is hydrogen, lower alkyl, halogen or lower alkoxycarbonylamino, with the proviso that when $R^3$ is lower alkyl, lower alkyl having phenyl or lower alkyl having piperidino, $R^2$ is cyclo(cyclo)alkyl, furyl or thienyl.

5. A compound of claim 4, wherein
n is an integer of 1.

6. A compound of claim 5, wherein
$R^3$ is hydrogen.

7. A compound of claim 6, wherein
$R^1$ is methyl,
$R^2$ is phenul, furyl, or thienyl, and
$R^3$, $R^4$ and $R^5$ are each hydrogen.

8. A compound of claim 7, which is 1-methyl-1-phenyl-1,2,3,4-tetrahydroisoquinoline or its hdrochloride.

9. A compound of claim 5, wherein
$R^2$ is thienyl,
$R^3$ is lower alkyl,
$R^4$ and $R^5$ are each hydrogen.

10. A compound of claim 5, wherein
$R^2$ is phenyl,
$R^3$ is lowr alkenyl, lower alkanoyl having halogen or lower alkanoyl having piperidino, and
$R^4$ and $R^5$ are each hydrogen.

11. A compound of claim 4,
wherein n is an integer of 2.

12. A compound of claim 11, wherein
$R^1$ is lower alkyl,
$R^2$ is phenyl,
$R^3$, $R^4$ and $R^5$ are each hydrogen.

13. An N-methyl-D-aspartate receptor antagonist A pharmaceutical composition comprising an effective amount of a compound of claim 1, as an active ingredient, in association with a pharmaceutically acceptable, substantially nontoxic carrier or excipient.

14. A method for the therapeutic treatmetn of convulsion and delayed neuronal death which comprises administering an effective amount of a compound of claim 1 to a human being or animal.

* * * * *